(12) United States Patent
Bae et al.

(10) Patent No.: US 12,144,685 B2
(45) Date of Patent: Nov. 19, 2024

(54) METHOD AND APPARATUS FOR QUANTITATIVE ULTRASOUND IMAGING USING SINGLE-ULTRASOUND PROBE

(71) Applicant: KOREA ADVANCED INSTITUTE OF SCIENCE AND TECHNOLOGY, Daejeon (KR)

(72) Inventors: Hyeon-Min Bae, Daejeon (KR); Myeong Gee Kim, Daejeon (KR); Gibbeum Lee, Daejeon (KR); Seokhwan Oh, Daejeon (KR); Youngmin Kim, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 366 days.

(21) Appl. No.: 17/115,939

(22) Filed: Dec. 9, 2020

(65) Prior Publication Data
US 2021/0177380 A1  Jun. 17, 2021

(30) Foreign Application Priority Data

Dec. 13, 2019 (KR) .................. 10-2019-0166617
Jul. 13, 2020 (KR) .................. 10-2020-0086059

(51) Int. Cl.
*A61B 8/08* (2006.01)
*A61B 8/00* (2006.01)
(Continued)

(52) U.S. Cl.
CPC ............ *A61B 8/5207* (2013.01); *A61B 8/145* (2013.01); *A61B 8/587* (2013.01); *G06N 3/08* (2013.01);
(Continued)

(58) Field of Classification Search
CPC ....... A61B 8/5207; A61B 8/145; A61B 8/587; G16H 50/50; G16H 30/40; G06N 3/08; G06T 11/005; G06T 2210/41
See application file for complete search history.

(56) References Cited

U.S. PATENT DOCUMENTS

| | | | |
|---|---|---|---|
| 6,248,994 B1 * | 6/2001 | Rose ................... | G01B 11/162 356/28 |
| 2012/0172724 A1 * | 7/2012 | Hill ....................... | A61B 8/12 600/443 |

(Continued)

FOREIGN PATENT DOCUMENTS

| JP | 2012-239546 | 12/2012 |
|---|---|---|
| JP | 6457157 | 1/2019 |

(Continued)

OTHER PUBLICATIONS

Jakovljevic M, Hsieh S, Ali R, Chau Loo Kung G, Hyun D, Dahl JJ. Local speed of sound estimation in tissue using pulse-echo ultrasound: Model-based approach. J Acoust Soc Am. Jul. 2018;144(1):254. doi: 10.1121/1.5043402. PMID: 30075660; PMCID: PMC6045494 (Year: 2018).*

(Continued)

*Primary Examiner* — John D Li
(74) *Attorney, Agent, or Firm* — LEX IP MEISTER, PLLC

(57) ABSTRACT

A method of operating an image device operated by at least one processor is provided. The method of operating an image device comprises generating beamformed RF-mode images including phase shift information for each incident angle by using multi-angle ultrasound-echo data, generating phase shift maps representing a displacement of speckle pattern between adjacent beamformed RF-mode images, and obtaining a speed-of-sound distribution image corresponding to the phase shift maps by using a deep neural network (Continued)

which is trained to reconstruct speed-of-sound distribution of a tissue from training phase shift maps.

6 Claims, 17 Drawing Sheets

(51) Int. Cl.
 *A61B 8/14* (2006.01)
 *G06N 3/08* (2023.01)
 *G06T 11/00* (2006.01)
 *G16H 30/40* (2018.01)
 *G16H 50/50* (2018.01)

(52) U.S. Cl.
 CPC ........... *G06T 11/005* (2013.01); *G16H 30/40* (2018.01); *G16H 50/50* (2018.01); *G06T 2210/41* (2013.01)

(56) References Cited

U.S. PATENT DOCUMENTS

| | | | |
|---|---|---|---|
| 2014/0364734 | A1 | 12/2014 | Huang |
| 2016/0317121 | A1* | 11/2016 | Frenz .................. A61B 8/14 |
| 2018/0185005 | A1 | 7/2018 | Sandhu et al. |
| 2019/0307427 | A1* | 10/2019 | Levy .................. A61B 6/5217 |
| 2020/0389658 | A1* | 12/2020 | Kim .................. H04N 19/172 |

FOREIGN PATENT DOCUMENTS

| | | |
|---|---|---|
| JP | 2021-133123 | 9/2021 |
| KR | 10-2007-0069322 | 7/2007 |
| KR | 10-2013-0080640 | 7/2013 |
| KR | 10-2067340 | 1/2020 |

OTHER PUBLICATIONS

Benjamin A, et al. Surgery for Obesity and Related Diseases: I. A Novel Approach to the Quantification of the Longitudinal Speed of Sound and Its Potential for Tissue Characterization. Ultrasound Med Biol. Dec. 2018;44(12):2739-2748. doi: 10.1016/j.ultrasmedbio. 2018.07.021. Epub Sep. 15, 2018. (Year: 2018).*

Myeong-Gee Kim et al., "Robust Single-Probe Quantitative Ultrasonic Imaging System With a Target-Aware Deep Neural Network", IEEE transaction on Bio. vol. 68, No. 12(Jun. 7, 2021).

Patrick Stahli et al., "Forward model for quantitative pulse-echo speed-of-sound imaging", arXiv:1902.10639v2, Jun. 24, 2019.

Sergio J Sanabria et al., "Spatial domain reconstruction for imaging speed-of-sound with pulse-echo ultrasound : simulation and in vivo study", Phys. Med. Biol. 63 (2018).

Micha Feigin et al., "A deep learning framework for single-sided sound speed inversion in medical ultrasound", IEEE Transactions on Biomedical Engineering, vol. 67 , Issue: 4, arXiv:1810.00322v4, Jul. 25, 2019. DOI: 10.1109/TBME.2019.2931195.

* cited by examiner

Incident 0° plane wave

Incident 15° plane wave

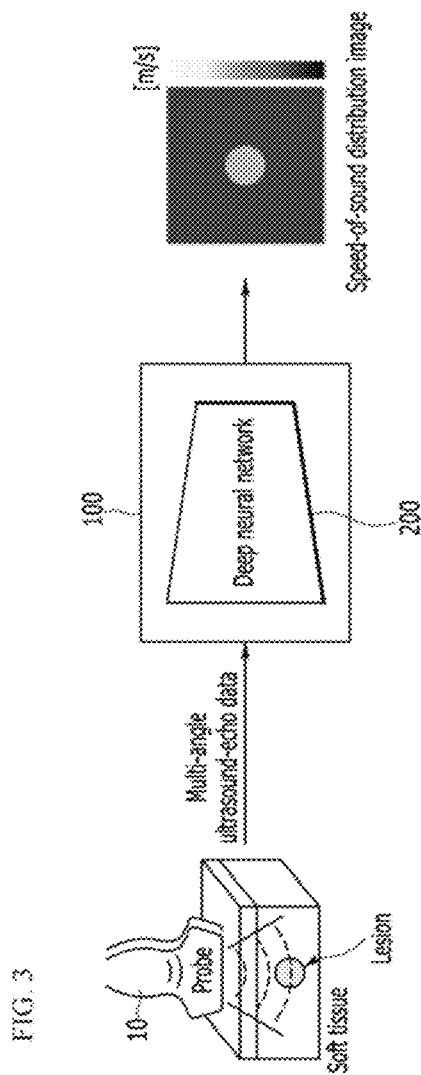

-15° angle

0° angle

15° angle

[-15°, -10°] angle

[-5°, 0°] angle

[10°, 15°] angle

METHOD AND APPARATUS FOR QUANTITATIVE ULTRASOUND IMAGING USING SINGLE-ULTRASOUND PROBE

CROSS-REFERENCE TO RELATED APPLICATION

This application claims priority to and the benefit of Korean Patent Application No. 10-2019-0166617 filed in the Korean Intellectual Property Office on Dec. 13, 2019, and Korean Patent Application No. 10-2020-0086059 filed in the Korean Intellectual Property Office on Jul. 13, 2020, the entire contents of which are incorporated herein by reference.

BACKGROUND

(a) Field

The present disclosure relates to an image reconstruction technology using ultrasounds.

(b) Description of the Related Art

Since it is difficult to detect a cancer early, periodic examinations are required and the size and characteristics of a lesion should be continuously monitored. Representative imaging equipment for this includes an X-ray, a magnetic resonance imaging (MRI), a computed tomography (CT), and an ultrasound. X-ray, MRI, and CT have a risk of radiation exposure and a drawback in that the measurement time is long and the cost is too high. In contrast, the ultrasound imaging equipment is safe and relatively inexpensive, and provides a real time image so that a user can obtain desired images while monitoring a lesion in real time.

Presently, a B-mode (brightness mode) imaging system is the most commercially available ultrasound imaging equipment. Since the B-mode imaging system can find a location of the lesion in real time, a user can effectively obtain desired images while monitoring the lesion in real time. In addition, since the B-mode imaging system is safe and relatively inexpensive, the B-mode imaging system has a good accessibility. However, the B-mode imaging system has drawbacks in that the quality of the obtained images may vary according to the proficiency of a user and quantitative characteristics cannot be imaged. That is, since the B-mode technique provides only geometric information of a tissue, sensitivity and specificity may be low in a differential diagnosis that distinguishes benign tumor and malignant tumor, which are classified by histological characteristics.

Recently, researches to obtain histological information by quantitatively imaging ultrasound characteristics of a tissue have been progressed. Pathological changes in tissues give rise to structural changes in cells, and representative techniques, which perform imaging the change in ultrasound characteristics of the corresponding tissue due to such structural changes, include Elastography and ultrasound computed tomography (USCT). The Elastography can quantitatively image the elasticity and stiffness of a tissue. However, the Elastography requires an additional dedicated device and consumes a lot of energy. Therefore, the Elastography can be applied only to expensive ultrasound equipment and is not suitable for imaging dynamically moving tissues due to a low frame rate. The ultrasound computed tomography makes available to obtain a high resolution quantitative image. However, since ultrasonic sensors should be placed to enclose an object, the ultrasound computed tomography is applied to imaging breast only and has a limitation in measuring various organs. In addition, imaging using the ultrasound computed tomography takes over one minute, so that to observe real time movement is impossible. Further, it is impossible to move the system due to the very large size thereof.

SUMMARY

An embodiment of the present disclosure provides a method and apparatus for quantitatively imaging using multi-angle ultrasound-echo data obtained by a single ultrasound probe.

Another embodiment of the present disclosure provides a method and apparatus that generates a phase shift map for each of the two adjacent incident angles using multi-angle ultrasound-echo data obtained by a single ultrasound probe and images a speed-of-sound (SoS) distribution by inputting the phase shift maps into a deep neural network.

Yet another embodiment of the present disclosure provides a target-aware deep neural network that reconstructs speed-of-sound distribution from phase shift maps by using geometric information of a target in a tissue as guide information.

According to an embodiment, a method of operating an image device operated by at least one processor may be provided. The method includes generating beamformed RF-mode images including phase shift information for each incident angle by using multi-angle ultrasound-echo data, generating phase shift maps representing a displacement of speckle pattern between adjacent beamformed RF-mode images, and obtaining a speed-of-sound distribution image corresponding to the phase shift maps by using a deep neural network which is trained to reconstruct speed-of-sound distribution of a tissue from training phase shift maps.

The multi-angle ultrasound-echo data may include data obtained by emitting plane waves having different incident angles into the tissue from a single ultrasound probe.

Obtaining the speed-of-sound distribution image may include inputting the phase shift maps and a geometric image including geometric information of a target tissue into the deep neural network, and obtaining the speed-of-sound distribution image output from the deep neural network. The deep neural network may reconstruct the speed-of-sound distribution of the target tissue from the phase shift maps by using the geometric image as guide information.

The geometric image may include an image obtained by segmenting a B-mode image generated from the multi-angle ultrasound-echo data into regions according to shape.

Generating the phase shift maps may include calculating a displacement between two sub-blocks with the largest cross-correlation among sub-blocks of two beamformed RF-mode images with adjacent incident angles, as the displacement of speckle pattern, and generating an image representing the displacement of speckle pattern as a phase shift map of the two beamformed RF-mode images.

The deep neural network may include an encoder that extracts features of input phase shift maps, and a decoder that reconstruct a high resolution image while upsampling a feature map transmitted from the encoder.

The decoder may receive an image including geometric image of a target tissue as guide information.

According to another embodiment, a method of operating an imaging device operated by at least one processor may be provided. The method may include receiving multi-angle ultrasound-echo data of a tissue and a speed-of-sound distribution image of the tissue as training data, and training a deep neural network to image a speed-of-sound distribution of the tissue from the multi-angle ultrasound-echo data by using the training data.

The multi-angle ultrasound-echo data may be obtained using a simulation tool or a phantom modeling the speed-of-sound distribution and scatters in the tissue.

The training data may further include a geographic image including geometric information of the tissue.

Training the deep neural network may include training the deep neural network to image speed-of-sound distribution of the tissue from the multi-angle ultrasound-echo data by using the geometric image as guide information.

Training the deep neural network may include generating beamformed RF-mode images including phase shift information for each incident angle by using the multi-angle ultrasound-echo data, generating phase shift maps representing a displacement of speckle pattern between adjacent beamformed RF-mode images, and training the deep neural network so as to minimize reconstruction loss by comparing a reconstruction result of features of the phase shift maps by the deep neural network with the speed-of-sound distribution image of the tissue.

Generating the phase shift maps may include calculating a displacement between two sub-blocks with the largest cross-correlation among sub-blocks of two beamformed RF-mode images with adjacent incident angles, as the displacement of speckle pattern, and generating an image representing the displacement of the speckle pattern as a phase shift map of the two beamformed RF-mode images.

The deep neural network may include an encoder that extracts features of input phase shift maps, and a decoder that reconstruct a high resolution image while upsampling a feature map transmitted from the encoder.

According to still another embodiment, a computing device may be provided. The computing device may include a memory that stores instructions of a program and a processor that generates a speed-of-sound distribution image of a target tissue from multi-angle ultrasound-echo data obtained from the target tissue by executing the instructions. The processor may transform a displacement of speckle pattern varying according to incident angles by using the multi-angle ultrasound-echo data and generates the speed-of-sound distribution image by reconstructing phase shift information included in the images.

The multi-angle ultrasound-echo data may include data obtained by emitting plane waves with different incident angles into a tissue from a single ultrasound probe.

The processor may generate beamformed RF-mode images for each incident angle by using the multi-angle ultrasound-echo data, generate phase shift maps representing a displacement of speckle pattern between adjacent beamformed RF-mode images, and generate the speed-of-sound distribution image by reconstructing features of the phase shift maps.

The processor may generate a geometric image including geometric information of the target tissue by using the multi-angle ultrasound-echo data, and reconstructs phase shift information included in the images by using the geometric image as guide information.

The processor may obtain a sound speed distribution image corresponding to the images by using a deep neural network trained to reconstruct the sound speed distribution from the images generated by the spot pattern displacement.

The processor may generate a B-mode image including geometric information from the multi-angle ultrasound-echo data and output the sound speed distribution image with being overlaid on the B-mod image.

According to an embodiment, imaging a quantitative speed-of-sound distribution can be performed by using an ultrasound probe and imaging device for B-mode imaging as it is. As a result, imaging is simplified and various organs measurable by the existing ultrasound imaging devices can be measured. Further, the ultrasound probe and the imaging device for B-mode imaging can replace a certain part of an expensive ultrasound imaging device and can be added to the previously manufactured ultrasound imaging device.

According to the embodiment, a tissue can be imaged in real time by using a single ultrasound probe and the performance difference according to the users' proficiency is small.

According to the embodiment, by guiding the geometric characteristics of a target to a reconstruction network layer of a deep neural network model, the contrast and accuracy of quantitative images can be improved and speed-of-sound characteristics can be securely reconstructed from the ultrasound-echo data obtained in noise environment.

According to the embodiment, since the speed-of-sound characteristics are reconstructed using relative phase shift (phase difference) between ultrasound-echo data acquired at adjacent incident angles, the speed-of-sound distribution can be securely obtained from a severely attenuated ultrasound-echo data or irregular strong ultrasound-echo data.

BRIEF DESCRIPTION OF THE DRAWINGS

FIG. 3 and FIG. 4 are conceptual diagrams for explaining a quantitative imaging device using a single ultrasound probe according to an embodiment.

FIGS. 12A, 12B, 12C, 12D, 12E, 12F, 13A, 13B and 3C are diagrams showing a result of quantitative image reconstruction using a deep neural network according to an embodiment.

DETAILED DESCRIPTION

Figure 1:
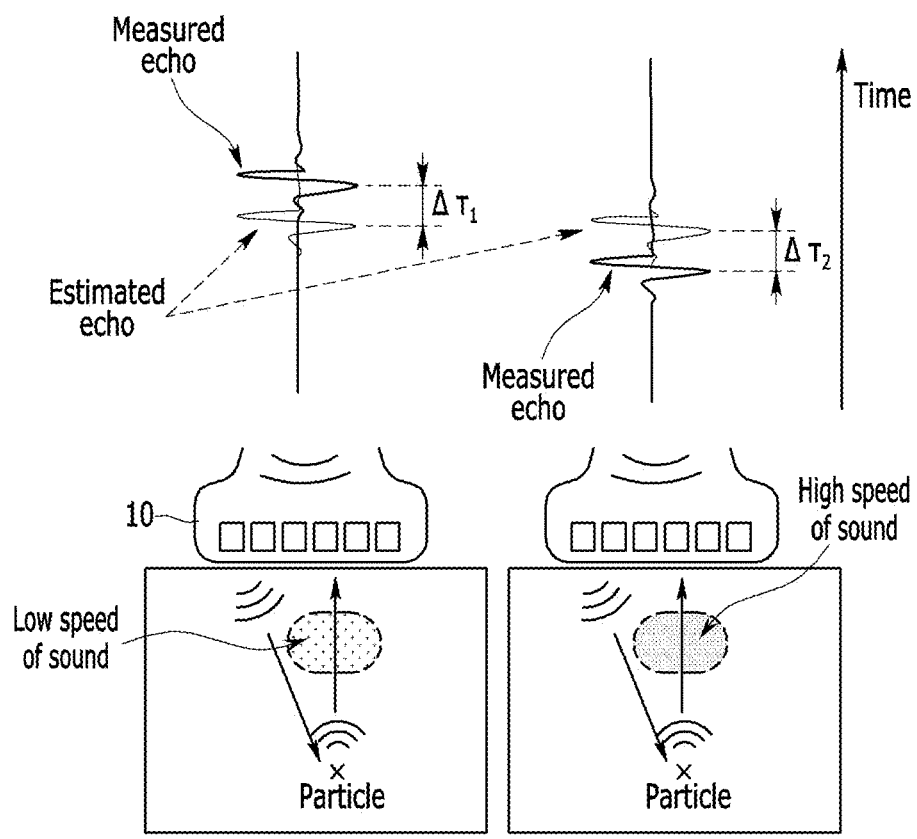
FIG. 1 is a diagram for explaining a phase shift according to a speed-of-sound distribution of a tissue.

In the following detailed description, exemplary embodiments of the present disclosure will be described in detail with reference to the accompanying drawings so that those of ordinary skill in the art may easily implement the present disclosure. However, the present disclosure may be implemented in various different forms and is not limited to the embodiments described herein. Accordingly, the drawings and description are to be regarded as illustrative in nature and not restrictive. Like reference numerals designate like elements throughout the specification.

As used herein, unless explicitly described to the contrary, the word "comprise", "include" or "have", and variations such as "comprises", "comprising", "includes", "including", "has" or "having" will be understood to imply the inclusion of stated elements but not the exclusion of any other elements. In addition, the term "unit", "-er", "-or" or "module" described in the specification mean a unit for processing at least one function and operation, and may be implemented by hardware components or software components, and combinations thereof.

A deep neural network of the present disclosure is an artificial intelligence model that learns at least one task and may be implemented as software/program executed in a computing device. The program is stored in a storage medium (non-transitory storage media) and includes instructions for executing operations of the present disclosure by a processor. The program may be downloaded via a network, or sold as a product.

FIG. 1 is a diagram for explaining a phase shift according to a speed-of-sound distribution of a tissue.

Referring to FIG. 1, a B-mode (brightness-mode) image provides a location and shape of a lesion in gray scale. The location and shape of the lesion are estimated using amplitude and phase shift (round-trip time) of an echo, which is obtained by reflection of emitted signal from an ultrasonic probe 10 at a focusing depth. At this time, the B-mode image is generated with amplitude obtained after applying a delay and sum (DAS) technique adapting an estimated phase shift to radio frequency (RF) data acquired in the ultrasound probe 10, under an assumption that speed-of-sound in a tissue is uniform.

However, the actual speed-of-sound in a tissue is not uniform. Thus, the speed-of-sound in some lesions may be slower than the average speed-of-sound in the tissue and that of other lesions may be faster than the average speed-of-sound in the tissue. That is, the phase shift occurs differently depending on the speed-of-sound distribution of the tissue, and information on such a phase shift is contained in the echo signal being a reflected signal.

Figure 2A:
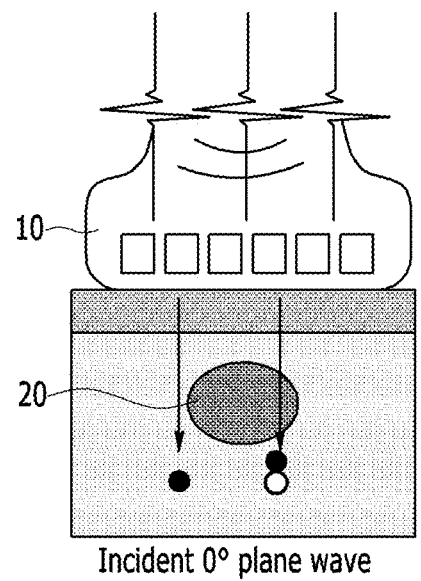
FIG. 2A and FIG. 2B are diagrams that conceptually explains imaging according to an incident angle.
Figure 2B:
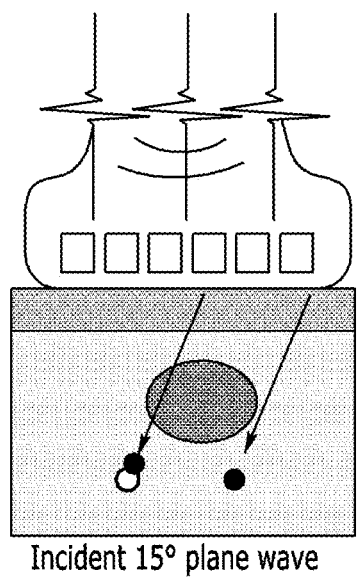

FIG. 2A and FIG. 2B are diagrams that conceptually explains imaging according to an incident angle.

Referring to FIG. 2A, FIG. 2A shows a case where an image is generated using ultrasound-echo data being a reflected signal when a plane wave is emitted from an ultrasonic probe 10 at an incident angle of 0°. FIG. 2B shows a case where an image is generated using ultrasound-echo data being a reflected signal when a plane wave is emitted from an ultrasonic probe 10 at an incident angle of 15°.

There are scatterers having a size smaller than the wavelength of sound wave in a tissue. The scatters are imaged as small speckles that appear as noise in an image. At this time, when there is a lesion 20 having a different speed-of-sound from a surrounding tissue, a speed-of-sound distribution in the tissue becomes non-uniform. Thus, the phase shifts of the reflected ultrasound-echo data get different according to the incident angles. Therefore, when imaging with ultrasound echo signals of different incident angles is performed, the locations of small speckles are imaged differently as shown in FIG. 2A and FIG. 2B.

As such, if the speed-of-sound distribution of the tissue is not uniform, the phase shifts are changed. Particularly, when imaging with ultrasound-echo data of different incident angles id performed, a speckle pattern changes even if in the same tissue. Hereinafter, an apparatus and method for imaging speed-of-sound distribution in a tissue using these characteristics will be described in detail.

Figure 4:
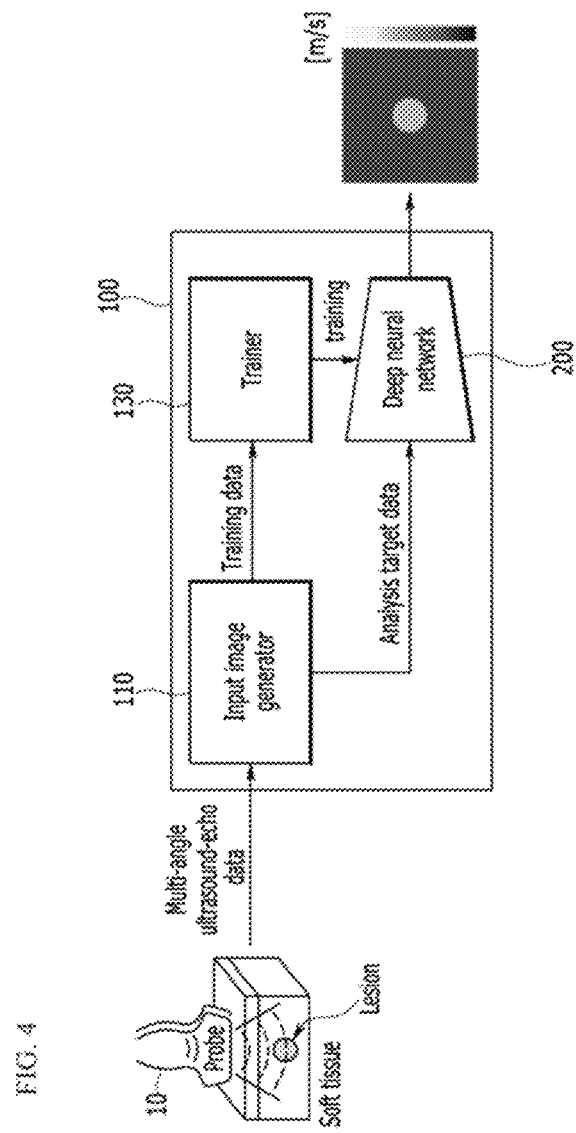

FIG. 3 and FIG. 4 are conceptual diagrams for explaining a quantitative imaging device using a single ultrasound probe according to an embodiment.

Referring to FIG. 3, the imaging device 100 is a computing device operated by at least one processor, which receives multi-angle ultrasound-echo data obtained by a single ultrasound probe 10 and performs imaging quantitative characteristics of a tissue using a deep neural network 200. In the description, the quantitative image is described using a speed-of-sound distribution image as an example.

The ultrasound probe 10 is a probe available for emitting ultrasound signal at various incident angles and obtaining ultrasound-echo data. The ultrasound probe 10 may be a general B-mode imaging probe. In the ultrasound probe 10, N piezoelectric elements are arranged, and the types of the ultrasound probe 10 may vary according to the arrangement form of the piezoelectric elements. For example, the ultrasound probe 10 may be a linear array probe or a curvilinear array probe. In addition, the ultrasound probe 10 may be a phased array probe that generates an ultrasound signal by applying electrical signals to each piezoelectric element at regular time intervals.

The ultrasound signal emitted from the ultrasound probe 10 may vary, such as a pulse with a single frequency, a chirp, or a continuous wave.

In the description, for ultrasound signal emitted at a specific incident angle, radio frequency (RF) data obtained by a plurality of piezoelectric elements are referred to as ultrasound-echo data of the specific incident angle. The ultrasound-echo data obtained at a plurality of incident angles is briefly referred to as multi-angle ultrasound-echo data. In the description, it is assumed that the multi-angle ultrasound-echo data includes ultrasound-echo data of seven different incident angles ($\theta1:\theta7$).

A B-mode image is an image generated with amplitude obtained through envelope detection of a waveform created from the obtained ultrasound-echo data.

An image created for each incident angle to acquire a phase shift map is generated with ultrasound-echo data obtained at a specific incident angle of the ultrasound probe, which, in order to distinguish from the B-mode image, may be referred to as a beamformed RF-mode image, briefly an RF-mode image, or an incident angle image, in the following description. In the description, in order to represent an image generated by applying a delay and sum (DAS) technique to ultrasound-echo data being RF data, the image generated for each incident angle is mainly referred to as the "beamformed RF-mode image". The beamformed RF-mode image is an image generated with phase shift information included in the RF data. Therefore, the beamformed RF-mode image is different from the B-mode image generated through envelope detection after applying the delay and sum (DAS) technique to the RF data.

The imaging device 100 mounts a trained deep neural network 200. Although training the deep neural network 200 may be performed in a separate device, it will be described that the imaging device 100 trains the deep neural network 200 for convenience of explanation.

Referring to FIG. 4, an imaging device 100 includes a deep neural network 200, and may include an input image generator 100 that generates input data for the deep neural network 200 by using multi-angle ultrasound-echo data and a trainer 130 that trains the deep neural network 200 using training data generated in the input image generator 110.

Upon receiving analysis target data generated in the input image generator 110, the trained deep neural network 200 reconstructs speed-of-sound characteristics included in the analysis target data and outputs a speed-of-sound distribution image.

Figure 5:
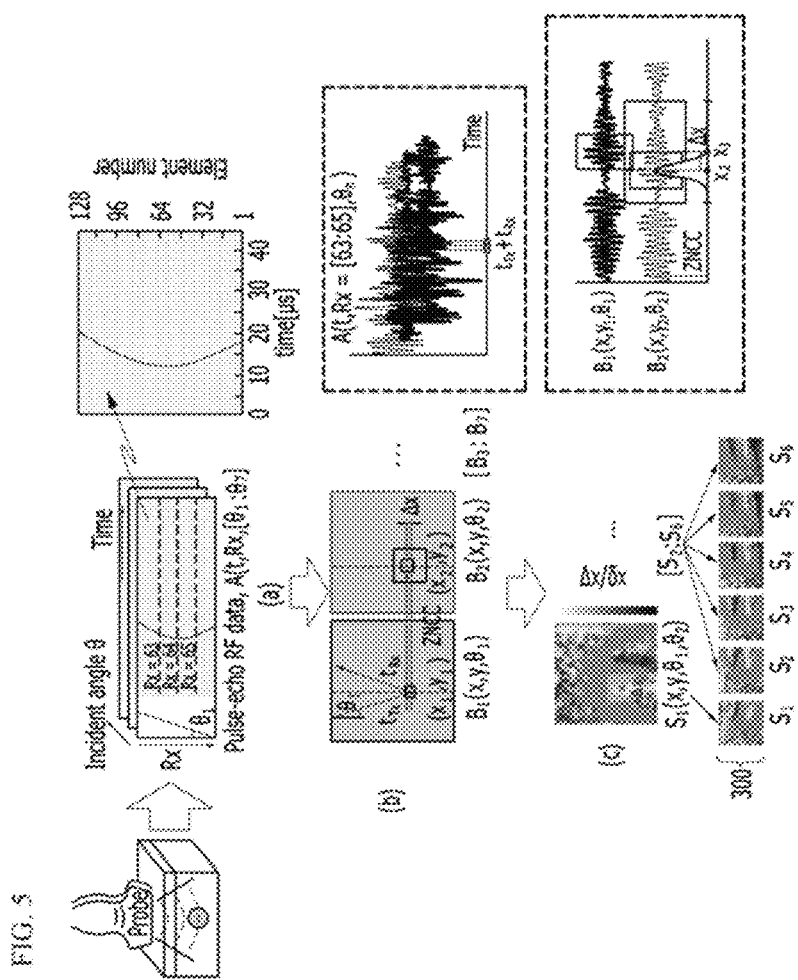
FIG. 5 is a diagram for explaining a method of generating an input image for a deep neural network.
Figure 6:
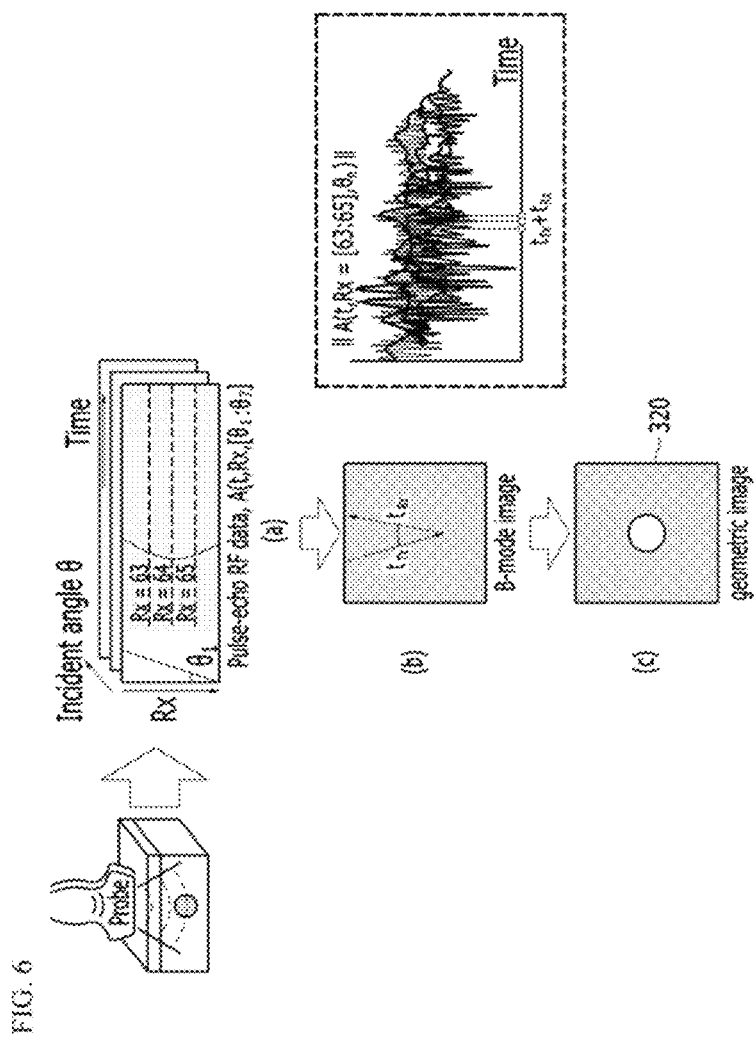
FIG. 6 is a diagram for explaining a method of generating a guide input image for a deep neural network.

FIG. 5 is a diagram for explaining a method of generating an input image for a deep neural network. FIG. 6 is a diagram for explaining a method of generating a guide input image for a deep neural network.

Referring to FIG. 5, the imaging device 100 may train the deep neural network 200 using images generated with multi-angle ultrasound-echo data. The imaging device 100 may train the deep neural network 200 using a two-dimensional phase shift map 300 that reflects phase shift information included in ultrasound-echo data of two adjacent incident angles.

Referring to (a) of FIG. 5, the imaging device 100 receives ultrasound-echo data A(t, Rx, [$\theta_1$:$\theta_7$]) which is obtained for each incident angle by emitting plane waves with different incident angles from the ultrasound probe 10. Here, t is time, Rx is transducer elements that have received ultrasound-echo data, and [$\theta_1$:$\theta_7$] is a plurality of incident angles. The ultrasound-echo data for each incident angle may be expressed as an image representing the receiving time for each element.

Referring to (b) of FIG. 5, the imaging device 100 generates beamformed RF-mode images $B_1(x, y, \theta_1)$, $B_2(x, y, \theta_2)$, and [$B_3$:$B_7$] using ultrasound-echo data for each incident angle. The beamformed RF-mode image may be a B-mode image of a specific incident angle. The imaging device 100 may generate a beamformed RF-mode image $B_n(x, y, \theta_n)$ of an incident angle $\theta_n$ using ultrasound-echo data A(t, Rx, $\theta_n$) for the corresponding incident angle, as shown in Equation 1. The beamformed RF-mode image $B_n(x, y, \theta_n)$ for the incident angle $\theta_n$ is generated from a delay and sum of the ultrasound-echo data A(t, Rx, $\theta_n$). Here, $t_{Tx}$ and $t_{Rx}$ are transmission delay and reception delay, and can be calculated as shown in Equation 2 and Equation 3, respectively.

$$B_n(x, y, \theta_n) = \sum_{R_x=1}^{N} A(t_{Tx} + t_{Rx}, Rx, \theta_n) \qquad \text{Equation 1}$$

$$t_{Tx} = ((x - \delta \cdot Tx)\sin\theta_n + y\cos\theta_n)/c_0 \qquad \text{Equation 2}$$

$$t_{Rx} = \sqrt{(x - \delta \cdot Rx)^2 + y^2} \Big/ c_0 \qquad \text{Equation 3}$$

In Equation 2 and Equation 3, $\delta$ is a pitch between the transducer elements receiving ultrasound-echo data, and $c_0$ is an average speed-of-sound of a tissue.

As described above with reference to FIG. 2, when comparing the beamformed RF-mode image $B_1$ and $B_2$ generated with ultrasound-echo data of different incident angles, it can be seen that there is a displacement in speckle pattern.

Referring to (c) of FIG. 5, the imaging device 100 transforms the displacement of speckle pattern between beamformed RF-mode images ($B_n(x, y, \theta_n)$, $B_{n+1}(x, y, \theta_{n+1})$) with adjacent incident angle into a phase shift map $S_n(x, y, \theta_n, \theta_{n+1})$ which is a two-dimensional image. The displacement of speckle pattern can be defined as a displacement of two sub-blocks having the largest cross-correlation among sub-blocks of two adjacent beamformed RF-mode images ($B_n$, $B_{n+1}$). The cross-correlation may be zero-normalized cross-correlation (ZNCC). The phase shift map $S_n$ is a two-dimensional image transformed from phase shift information that is included in the ultrasound-echo data obtained at two adjacent incident angles.

The imaging device 100 may create phase shift maps $S_1$, $S_2$, . . . , and $S_6$ from beamformed RF-mode images $B_1$, $B_2$, . . . , and $B_7$. The phase shift maps $S_1$, $S_2$, . . . , and $S_6$ is used as an input image for a deep neural network 200.

Referring to FIG. 6, a deep neural network 200 reconstructs a speed-of-sound distribution from the phase shift maps $S_1$, $S_2$, . . . , and $S_6$, and may use geometric characteristics of a target as guide information. To do this, the imaging device 100 detects an envelope of ultrasound-echo data A(t, Rx, [$\theta_1$:$\theta_7$]) obtained as (a) of FIG. 6, and generates a B-mode image as shown in (b) of FIG. 6.

Referring to (c) of FIG. 6, the imaging device 100 extracts structural/geometric information from the B-mode image and generates a geometric image 400 including location and shape information of a target. The imaging device 100 may generate a geometric image 320 from a B-mode image through various methods. For example, the imaging device 100 may generate the geometric image 320 through a gradient vector flow (GVF) algorithm. The geometric image 320 may be a binary image of a B-mode image or a segmented image divided into regions.

Figure 7:
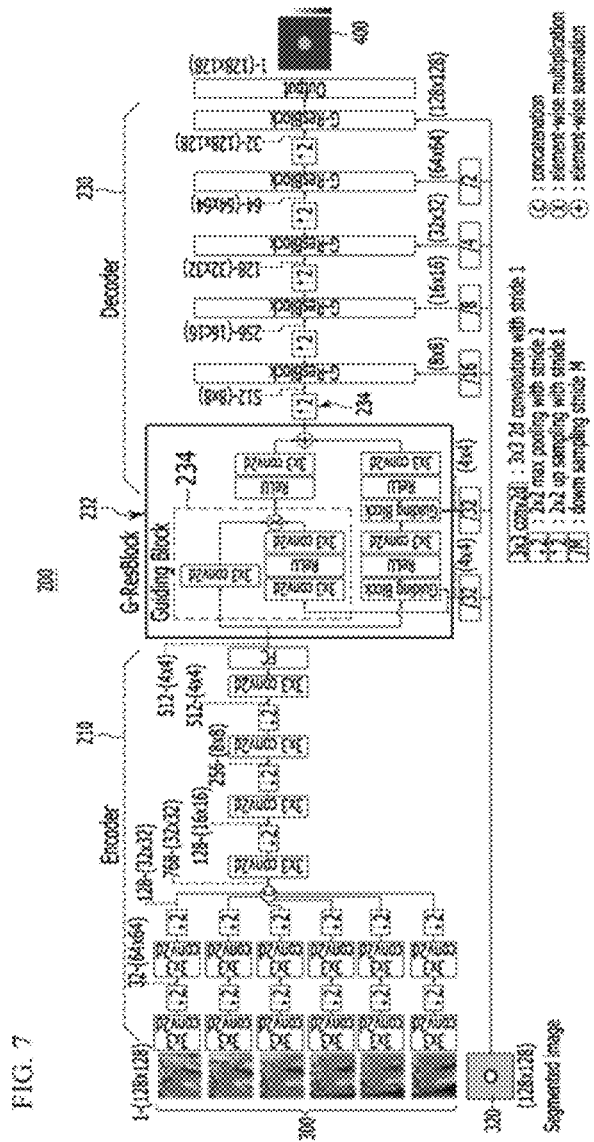
FIG. 7 is a configuration diagram of a deep neural network according to an embodiment.

FIG. 7 is a configuration diagram of a deep neural network according to an embodiment.

Referring to FIG. 7, a deep neural network 200 for ultrasound imaging is an artificial intelligence model capable of learning at least one task and may be implemented as software/program executed in a computing device. The deep neural network 200 includes an encoder 210 encoding features of input images 300, and a decoder 230 that decodes (reverse rendering) a feature map generated by the encoder 210 to reconstruct a speed-of-sound distribution image 400.

The encoder 210 receives input from a plurality of channels and the input images 300 may be the phase shift maps ($S_1$, $S_2$, . . . , $S_6$) described with reference to FIG. 5. The number of phase shift maps (the number of channels) may vary depending on the number of incident angles from the ultrasound probe. Meanwhile, the input images 300 may be beamformed RF-mode images generated with multi-angle ultrasound-echo data, but it is explained that the phase shift maps providing better performance are used. The phase shift map is a two-dimensional image representing a displacement of speckle pattern between adjacent beamformed RF-mode images, and the size of the images may be determined variously.

The encoder 210 may include at least one convolution layer for extracting quantitative features from each phase shift map, and convolution layers for extracting features of integrated input after integrating feature maps of each phase shift map. The convolution layers spatially encode the input while analyzing the quantitative features generated with a correlation between each phase shift map.

For example, each of the phase shift map with a size of 128×128 may be encoded as 128 feature maps with a size of 32×32, through a 2d convolution layer with a size of 3×3 and a max pooling layer with a size of 2×2, and a following 2d convolution layers with a size of 3×3 and a following max pooling layer with a size of 2×2. The feature maps (768-32×32) integrating feature maps (128-32×32) for each channel may be encoded as 512 feature maps with a size of 32×32, through a 2d convolution layer with a size of 3×3 and a max pooling layer with a size of 2×2, a 2d convolution layer with a size of 3×3 and a max pooling layer with a size of 2×2, a 2d convolution layer with a size of 3×3, and a fully connected layer (FC). An output of a fully connected layer 222 is transmitted to a decoder 230.

The decoder 230 receives the feature map output from the encoder 210, and gradually reconstructs a high resolution image while upsampling low resolution input, and outputs a speed-of-sound distribution image 400. At this time, the decoder 230 receives a geometric image 400 including location and shape information of a target, as guide information (priori information), and can reconstruct the speed-of-sound distribution more precisely and accurately by using the guide information. The geometric image 400 may be a binary mask image of a B-mode image including geometric information.

Reconstruction network layers of the decoder 230 may include at least one residual block (ResBlock) 232 and an upsampling layer 234 with the size of 2×2. The geometric image 400 described in FIG. 6 is downsampled to fit the input size of each residual block, and then input into the corresponding residual block for coarse-to-fine guiding. The residual block 232 can be referred to as a guided residual block (Guided ResBlock, G-ResBlock).

Through the guiding block 234, the residual block 232 may combine quantitative features transmitted from the encoder 210 and geometric information which is input as guide information. For example, the residual block 232 may have a structure combining a path made of one unit block including the guiding block and a path made of two unit blocks. Each unit block may include a guiding block, a ReLU, and a 2d convolution layer with the size of 3×3.

As described above, since the decoder 230 uses the geometric information of the target as guide information to reconstruct quantitative features, the contrast and accuracy of the speed-of-sound distribution image 400 can be improved.

The deep neural network 200 may learn to minimize reconstruction loss. The trainer 130 can train the deep neural network 200 using training data. A loss function Ll2 may be defined as, for example, Equation 4.

$$L_{l2} = E_{u,y}[\|c \cdot y - c \cdot G(u,c)\|_2]$$ Equation 4

In Equation 4, c ($c \in C \sim R^{128 \times 128}$) is a binary mask representing the spatial location of a lesion, y is a ground truth label, and G(u,c) is an output of the deep neural network 200 which receives c and u, and u may be a phase shift map of 6 channels.

Figure 8A:
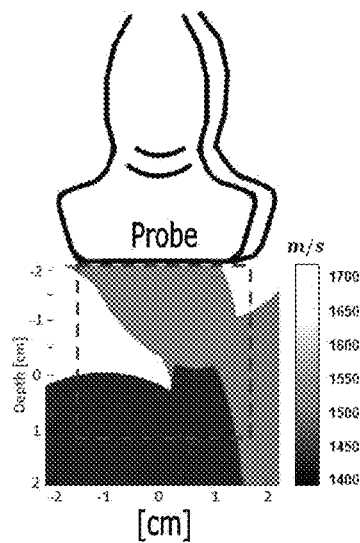
FIG. 8A and FIG. 8B are diagrams for explaining a method of obtaining training data according to an embodiment.
Figure 8B:
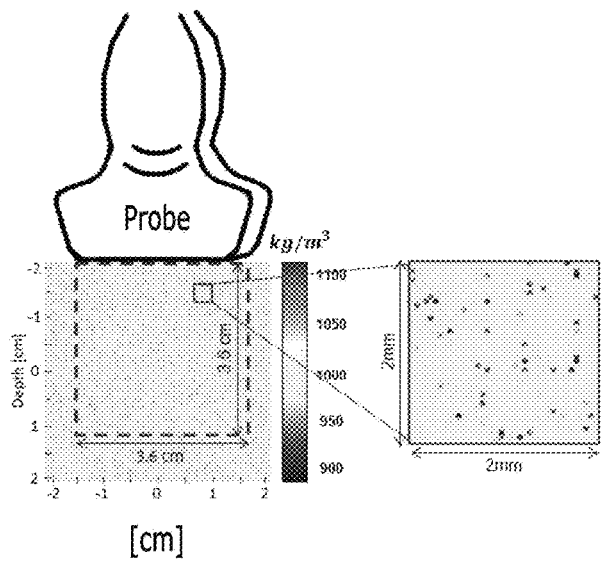

FIG. 8A and FIG. 8B are diagrams for explaining a method of obtaining training data according to an embodiment.

Referring to FIG. 8A and FIG. 8B, training data of the deep neural network 200 may include ultrasound-echo data obtained in various human body environments, and may be obtained using an ultrasound simulation tool (e.g., k-wave toolbox in Matlab).

Referring to FIG. 8A, simulation phantoms representing organs and lesions models the sound speed distribution so as to maintain generality and simplicity while simulating the human body. For example, an ellipse having a sound speed of 1400 m/s to 1700 m/s may be placed on an arbitrary location inside a region of interest with an arbitrary size. The region of interest may be set, for example, with a size of 36 mm×36 mm.

Referring to FIG. 8B, scatters of a tissue are modeled in the ultrasound simulation tool. For example, 50,000 scatters may be placed with a uniform distribution in a density domain. A background density (mass density) and an attenuation coefficient may be 1000 kg/m³ and 0.5 dB/MHz/cm, respectively.

FIGS. 9A, 9B, 9C, 9D, 9E and 9F are diagrams for explaining a method of generating a phase shift map from multi-angle ultrasound-echo data according to an embodiment.

Referring to FIGS. 9A, 9B, 9C, 9D, 9E and 9F, ultrasound-echo data may be obtained using a plane wave having multi-incident angles. For example, the angles may be −15°, −10 , −5, 0°, 5°, 10°, and 15°.

Figure 9A:
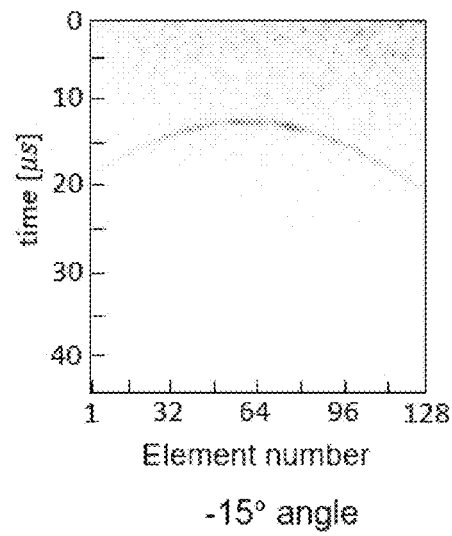
FIGS. 9A, 9B, 9C, 9D, 9E and 9F are diagrams for explaining a method of generating a phase shift map from multi-angle ultrasound-echo data according to an embodiment.
Figure 9B:
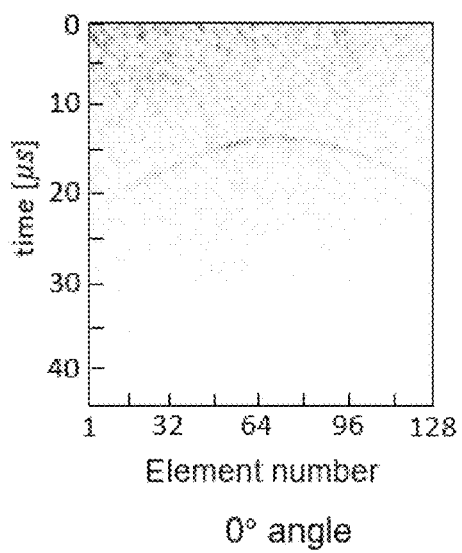
Figure 9C:
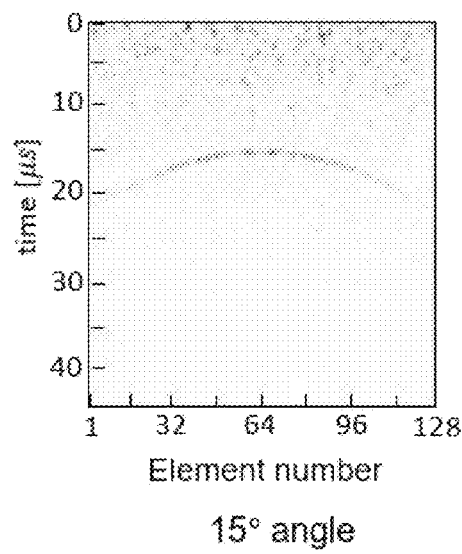

Referring to FIGS. 9A, 9B and 9C are images representing ultrasound-echo data obtained by receiving elements (element number) according to time at an incident angles of −15°, 0°, and 15°, respectively. Beamformed RF-mode images are generated using phase shift information of ultrasound-echo data for each incident angle.

Figure 9D:
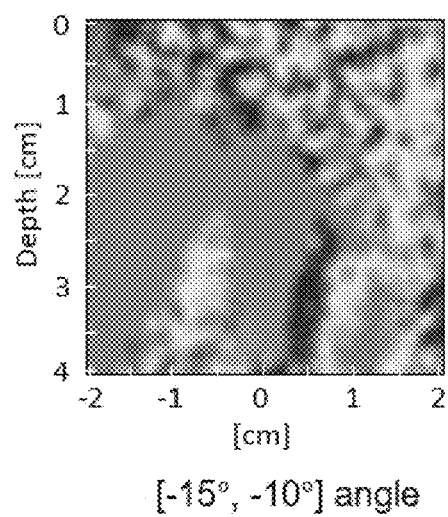
Figure 9E:
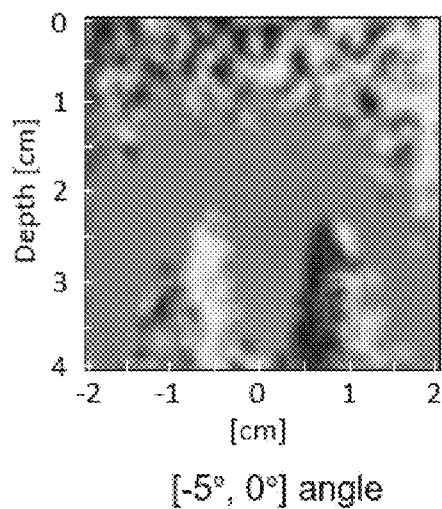
Figure 9F:
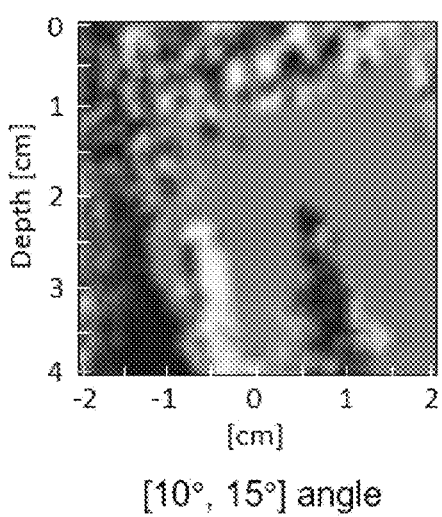

Referring to FIGS. 9D, 9E and 9F are two-dimensional images representing displacements of the speckle patterns between beamformed RF-mode images with adjacent incident angles.

Figure 10:
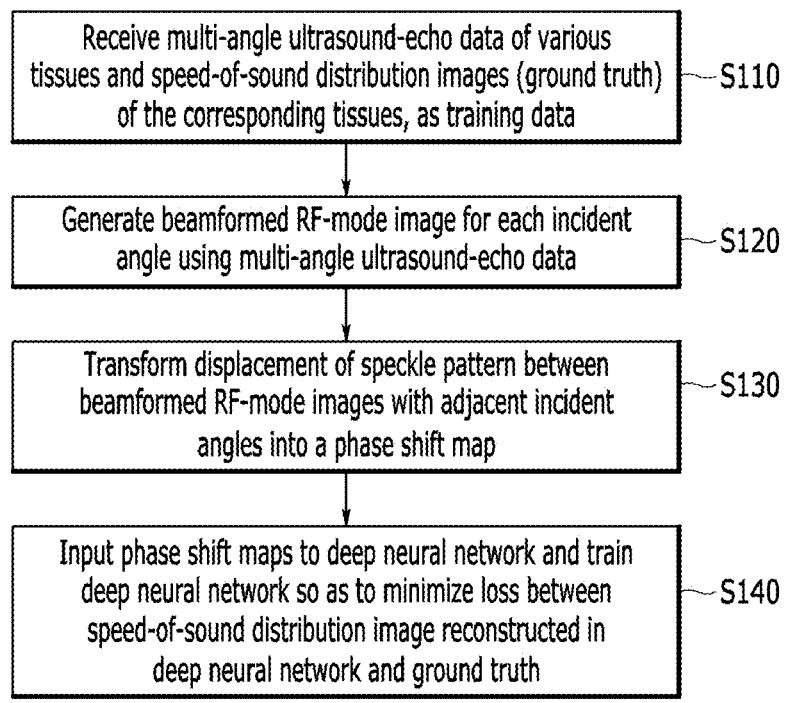
FIG. 10 is a flowchart showing a training method of a deep neural network according to an embodiment.

FIG. 10 is a flowchart showing a training method of a deep neural network according to an embodiment.

Referring to FIG. 10, an imaging device 100 receives multi-angle ultrasound-echo data of various tissues and speed-of-sound distribution images (ground truth) of the corresponding tissues, as training data (S110). The multi-angle ultrasound-echo data is ultrasound-echo data obtained for each incident angle by emitting plane waves having different incident angles into a tissue, and may be collected using an ultrasound simulation tool. Here, the multi-angle ultrasound-echo data for training may be obtained using simulation phantoms modeling the speed-of-sound distribution and scatters in the tissue. A speed-of-sound distribution image of the tissue may be the speed-of-sound distribution image of the simulation phantoms.

Meanwhile, the training data may further include a geometric image including geometric information of the tissue.

The imaging device 100 generates a beamformed RF-mode image for each incident angle using multi-angle ultrasound-echo data (S120). The beamformed RF-mode image is an image generated using phase shift information of ultrasound-echo data obtained at a specific incident angle, and may be generated by applying a delay and sum (DAS) technique to ultrasound-echo data.

The imaging device 100 transforms a displacement of speckle pattern between beamformed RF-mode images with adjacent incident angles into a phase shift map being a two-dimensional image (S130).

The imaging device 100 inputs the phase shift maps to a deep neural network 200 having an encoder-decoder structure, and trains the deep neural network 200 so as to minimize a loss between the speed-of-sound distribution image reconstructed in the deep neural network 200 and the ground truth (S140). At this time, if the deep neural network 200 is a target-aware deep neural network that receives a geometric image of a tissue as guide information and reconstructs the received image, the imaging device 100 may generate a geometric image to fit an input size of the decoder block and may input the geometric image as guide information of the corresponding decoder block. The deep neural network 200 may be trained to reconstruct the speed-of-sound distribution from features of the phase shift maps while recognizing locations and regions with different speed-of-sound through the geometric images.

Figure 11:
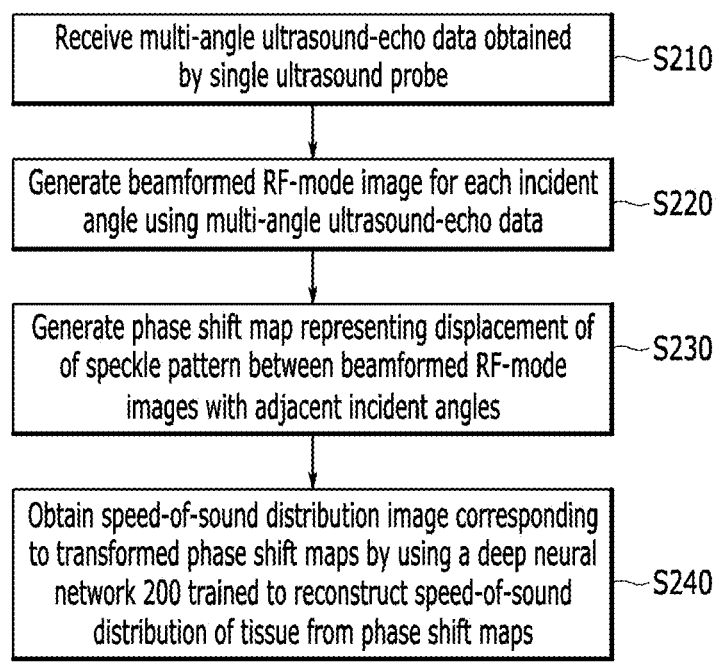
FIG. 11 is a flowchart showing a quantitative imaging method according to an embodiment.

FIG. 11 is a flowchart showing a quantitative imaging method according to an embodiment.

Referring to FIG. 11, an imaging device 100 receives multi-angle ultrasound-echo data obtained by a single ultrasound probe 10 (S210). The multi-angle ultrasound-echo data is ultrasound-echo data obtained for each incident angle by emitting plane waves having different incident angles into a tissue, and may be collected by a single ultrasound probe 10.

The imaging device 100 generates a beamformed RF-mode image for each incident angle using multi-angle ultrasound-echo data (S220). The beamformed RF-mode image is an image generated using phase shift information of ultrasound-echo data obtained at a specific incident angle, and may be generated by applying a delay and sum (DAS) technique to ultrasound-echo data. At this time, the imaging device 100 may generate a geometric image, which is guide information used in quantitative image reconstruction. The geometric image may be a binary mask of a B-mode image generated using multi-angle ultrasound-echo data.

The imaging device 100 generates a phase shift map representing a displacement of speckle pattern between beamformed RF-mode images having adjacent incident angles (S230).

The imaging device 100 obtains a speed-of-sound distribution image corresponding to a transformed phase shift maps, by using a deep neural network 200 trained to reconstruct the speed-of-sound distribution of the tissue from the phase shift maps (S240).

If the deep neural network 200 is a target-aware deep neural network that receives the geometric image of the tissue as guide information and reconstructs the received image, the imaging device 100 may input the geometric image into the deep neural network 200 along with the phase shift maps and may obtain a quantitative speed-of-sound distribution image which is reconstructed with a guidance of the geometric image. The imaging device 100 may output a speed-of-sound distribution image with being overlaid on a B-mode image including geometric information.

FIGS. 12A, 12B, 12C, 12D, 12E, 12F, 13A, 13B and 3C are diagrams showing a result of quantitative image reconstruction using a deep neural network according to an embodiment.

Figure 12A:
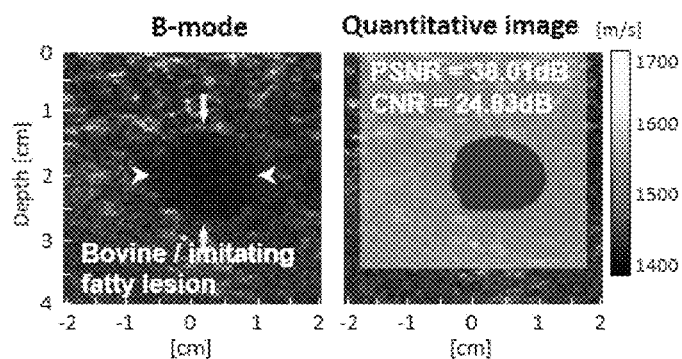
Figure 12B:
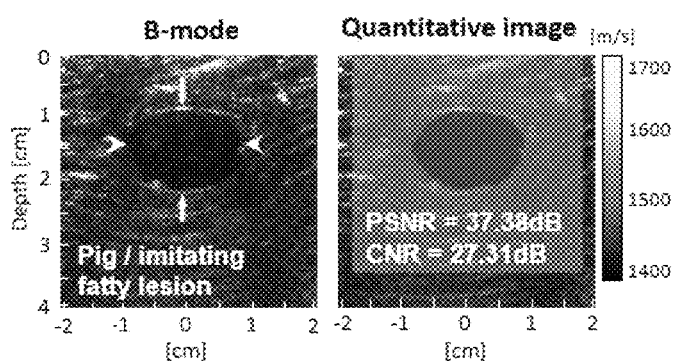

FIGS. 12A and 12B are reconstruction results of quantitative speed-of-sound distribution image obtained by the imaging device 10, based on multi-angle ultrasound-echo data obtained from a phantom. Here, the phantom is created by inserting objects imitating lipoma, benign tumors, and malignant tumors into beef and pork.

Figure 12C:
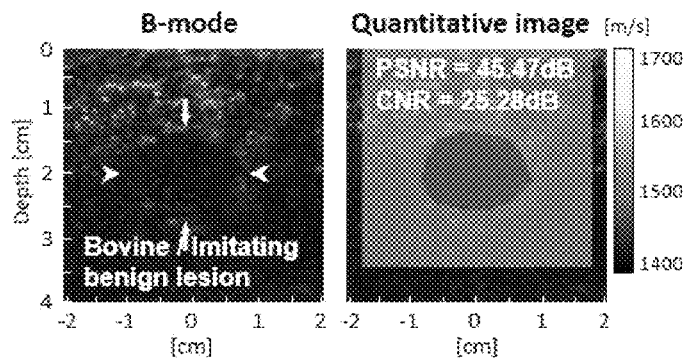
Figure 12D:
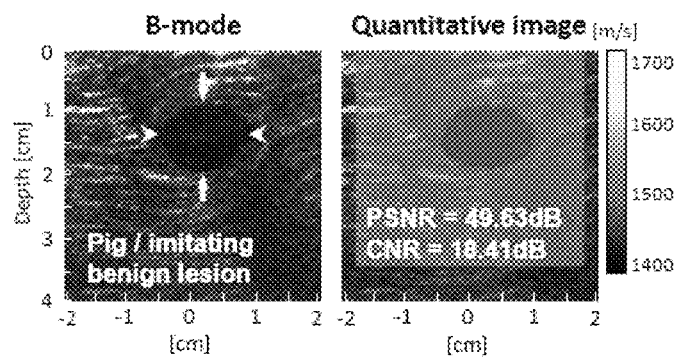
Figure 12E:
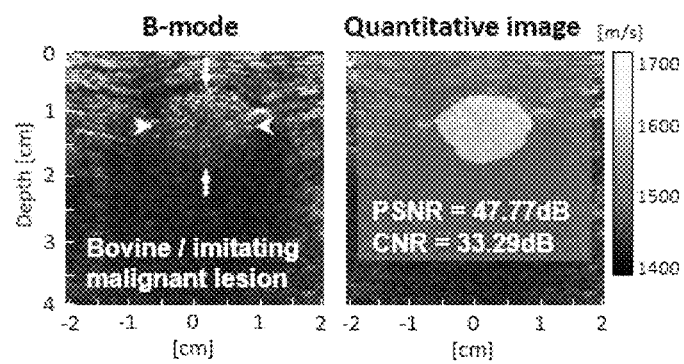
Figure 12F:
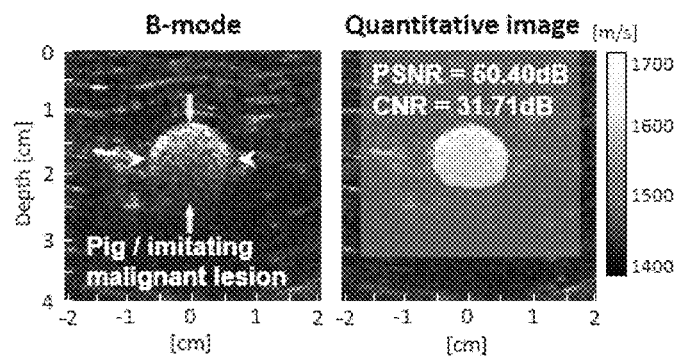

Each of FIG. 12A and FIG. 12B is a result that a phantom with an object imitating lipoma inserted into beef and pork is reconstructed as a B-mode image and a quantitative image. Each of FIG. 12C and FIG. 12D is a result that a phantom with an object imitating benign tumors inserted into beef and pork is reconstructed as a B-mode image and a quantitative image. Each of FIG. 12E and FIG. 12F is a result that a phantom with an object imitating malignant tumors inserted into beef and pork is reconstructed as a B-mode image and a quantitative image.

Existing imaging devices provide only B-mode images, but the imaging device 100 may provide a quantitative speed-of-sound distribution image which cannot be obtained from existing B-mode images. Not only can a location and shape of a lesion be obtained from the speed-of-sound distribution image, but also histological information can be obtained from the speed-of-sound. Furthermore, the imaging device 100 may distinguish the lesion from the speed-of-sound distribution image, according to speed-of-sound characteristics of lipoma, benign tumors, and malignant tumors.

Figure 13A:
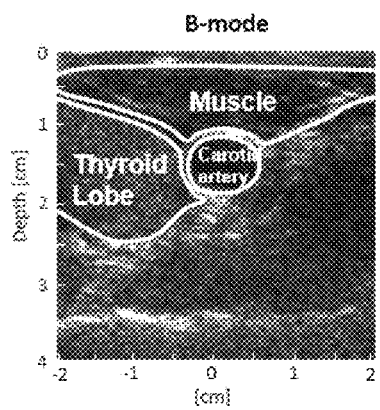
Figure 13B:
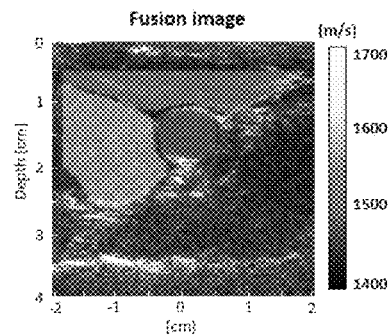
Figure 13C:
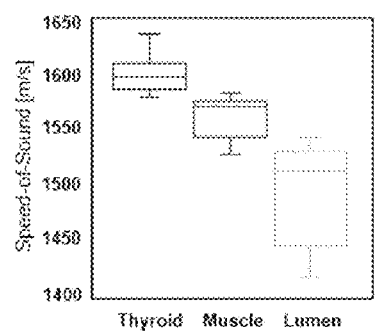

FIGS. 13A, 3B and 13C show results of reconstructing a quantitative speed-of-sound image of carotid artery, neck muscles and thyroid for 10 normal persons and then comparing values thereof. FIG. 13A shows an existing B-mode image, FIG. 13B shows a quantitative speed-of-sound distribution image reconstructed by the imaging device 100, and FIG. 13C shows a quantitative speed-of-sound value of thyroid, muscle and carotid arteries of 10 normal persons.

In comparison with the existing B-mode image, the imaging device 100 may further provide a quantitative speed-of-sound distribution image. The imaging device 100 may output a speed-of-sound distribution image with being overlaid on the B-mode image.

It can be seen that each organ may be classified with quantitative numerical values through the speed-of-sound distribution image.

Figure 14:
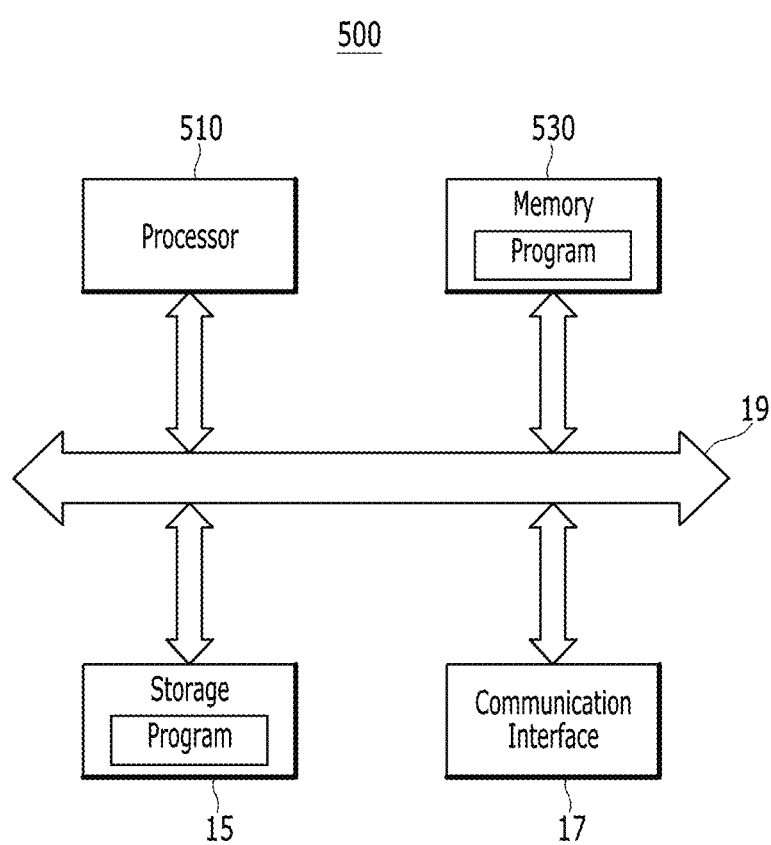
FIG. 14 is a configuration diagram of a computing device according to an embodiment.

FIG. 14 is a configuration diagram of a computing device according to an embodiment.

Referring to FIG. 14, the imaging device 100 may be a computing device 500 operated by at least one processor, and is connected with an ultrasound probe 10 or a device providing data obtained by the ultrasound probe 10.

The computing device 500 may include at least one processor 510, a memory 530 for loading a program executed by the processor 510, a storage 550 for storing programs and various data, a communication interface 570, and a bus 590 connecting them. In addition, the computing device 500 may further include various elements. When the program is loaded on the memory 530, the program may include instructions that make the processor 510 to perform methods/operations according to various embodiments of the present disclosure. That is, the processor 510 may perform methods/operations according to various embodiments of the present disclosure by executing instructions. The instructions are a series of computer readable instructions grouped by a function, which refers to elements of the computer program and being executed by a processor.

The processor 510 controls the overall operation of each elements of the computing device 500. Processor 510 may include at least one of a central processing unit (CPU), a micro processor unit (MPU), a micro controller unit (MCU), a graphic processing unit (GPU), or any type of processor well known in the art to which the present disclosure pertains. Further, the processor 510 may perform calculations for at least one application or program to execute methods/operations according to various embodiments of the present disclosure.

The memory 530 stores various data, instructions and/or information. The memory 530 may load at least one program from the storage 550 in order to perform methods/operations according to various embodiments of the present disclosure. The memory 530 may be implemented with a volatile memory such as RAM, but the technical range of the present disclosure is not limited thereto.

The storage 550 may store programs non-temporarily. The storage 550 may include a non-volatile memory, such as a read only memory (ROM), an erasable programmable ROM (EPROM), an electrically erasable programmable ROM (EEPROM), a flash memory, or any form of computer-readable recording medium well known in the art to which the present disclosure pertains.

The communication interface 570 supports wired/wireless communication of the computing device 500. To this end, the communication interface 570 may include a communication module well known in the technical field of the present disclosure.

The bus 590 provides a communication function between the elements of the computing device 500. The bus 590 may be implemented as various forms of buses, such as an address bus, a data bus, and a control bus.

As described above, according to the embodiment, imaging a quantitative speed-of-sound distribution can be performed by using an ultrasound probe and imaging device for B-mode imaging as it is. As a result, imaging is simplified and various organs measurable by the existing ultrasound imaging devices can be measured. Further, the ultrasound probe and the imaging device for B-mode imaging can replace a certain part of an expensive ultrasound imaging device and can be added to the previously manufactured ultrasound imaging device.

According to the embodiment, a tissue can be imaged in real time by using a single ultrasound probe and the performance difference according to the users' proficiency is small.

According to the embodiment, by guiding the geometric characteristics of a target to a reconstruction network layer of a deep neural network model, the contrast and accuracy of quantitative images can be improved and speed-of-sound characteristics can be securely reconstructed from the ultrasound-echo data obtained in noise environment.

According to the embodiment, since the speed-of-sound characteristics are reconstructed using relative phase shift (phase difference) between ultrasound-echo data acquired at adjacent incident angles, the speed-of-sound distribution can be securely obtained from a severely attenuated ultrasound-echo data or irregular strong ultrasound-echo data.

The embodiments of the present disclosure described above are not implemented through only the apparatus and the method, but may also be implemented through a program that realizes functions corresponding to the configuration of the embodiments of the present disclosure or a recording medium on which the program is recorded.

While this disclosure has been described in connection with what is presently considered to be practical embodiments, it is to be understood that the disclosure is not limited to the disclosed embodiments, but, on the contrary, is intended to cover various modifications and equivalent arrangements included within the spirit and scope of the appended claims.

What is claimed is:

1. A method of operating an image device operated by at least one processor, the method comprising:
generating beamformed RF-mode images including phase shift information for each incident angle by using multi-angle ultrasound-echo data;
generating phase shift maps representing a displacement of speckle pattern between adjacent beamformed RF-mode images; and
obtaining a speed-of-sound distribution image corresponding to the phase shift maps by using a deep neural network which is trained to reconstruct speed-of-sound distribution of a tissue from training phase shift maps, the speed-of-sound distribution image representing a quantitative speed-of-sound value at each position within the speed-of-sound distribution image,
wherein the deep neural network comprises:
an encoder configured to output a feature map by extracting quantitative features from the phase shift maps; and
a decoder configured to receive the feature map output from the encoder and a geometric image of a target tissue, and reconstruct the speed-of-sound distribution image from the feature map by using the geometric image as guide information, the decoder comprising
a plurality of blocks configured to combine the feature map output from the encoder with geometric information included in the geometric image, each of the plurality of blocks being further configured to combine an upsampled output of a preceding block among the plurality of blocks with the geometric information included in the geometric image, the geometric image being downsampled to fit an input size of a corresponding block among the plurality of blocks, and
a plurality of upsampling layers each configured to upsample an output of the preceding block, the upsampled output of the preceding block being input to a block succeeding the preceding block among the plurality of blocks.

2. The method of claim 1, wherein the multi-angle ultrasound-echo data includes data obtained by emitting plane waves having different incident angles into the tissue from a single ultrasound probe.

3. The method of claim 1, wherein the geometric image includes an image obtained by segmenting a B-mode image generated from the multi-angle ultrasound-echo data into regions according to shape.

4. The method of claim 1, wherein generating the phase shift maps comprises:
calculating a displacement between two sub-blocks with the largest cross-correlation among sub-blocks of two beamformed RF-mode images with adjacent incident angles, as the displacement of speckle pattern; and
generating an image representing the displacement of speckle pattern as a phase shift map of the two beamformed RF-mode images.

5. The method of claim 1, wherein
the decoder is further configured to reconstruct a high resolution image while upsampling outputs of the plurality of blocks.

6. The method of claim 1, wherein the geometric image is generated from a B-mode image including the geometric information.

* * * * *